(12) United States Patent
Fisher et al.

(10) Patent No.: US 6,762,832 B2
(45) Date of Patent: Jul. 13, 2004

(54) METHODS AND SYSTEMS FOR CONTROLLING THE CONCENTRATION OF A COMPONENT IN A COMPOSITION WITH ABSORPTION SPECTROSCOPY

(75) Inventors: Matthew L. Fisher, Allen, TX (US); David L. Snyder, Princeton, TX (US); Ashutosh Misra, Plano, TX (US)

(73) Assignee: Air Liquide America, L.P., Houston, TX (US)

( * ) Notice: Subject to any disclaimer, the term of this patent is extended or adjusted under 35 U.S.C. 154(b) by 117 days.

(21) Appl. No.: 10/064,222

(22) Filed: Jun. 21, 2002

(65) Prior Publication Data

US 2003/0020907 A1 Jan. 30, 2003

Related U.S. Application Data

(60) Provisional application No. 60/305,858, filed on Jul. 18, 2001.

(51) Int. Cl.[7] .................................................. G01J 3/42
(52) U.S. Cl. ........................................ 356/300; 438/16
(58) Field of Search .................................. 356/319, 323, 356/325, 326, 328, 300; 438/16

(56) References Cited

U.S. PATENT DOCUMENTS

3,987,808 A * 10/1976 Carbonell et al. .............. 137/3
6,507,397 B1 * 1/2003 Nishio et al. ................ 356/319

* cited by examiner

Primary Examiner—F. L. Evans
(74) Attorney, Agent, or Firm—Elwood L. Haynes

(57) ABSTRACT

Provided are methods and systems for controlling the concentration of a component in a composition, and semiconductor processing methods and systems. One exemplary method of controlling the concentration of a component in a composition involves: providing a composition which has a liquid portion, wherein the liquid portion contains a component to be monitored; performing an absorption spectroscopy measurement on a sample of the composition; and controlling the concentration of the component in the composition based on the absorption spectroscopy measurement using a feedback control loop. The invention allows for controlling the concentration of a component in a composition, for example, a corrosion inhibitor in a chemical planarization (CMP) chemical, as well as in pre- and post-CMP storage/treatment chemicals, and can provide real time, accurate process control in a simple and robust manner.

14 Claims, 5 Drawing Sheets

METHODS AND SYSTEMS FOR CONTROLLING THE CONCENTRATION OF A COMPONENT IN A COMPOSITION WITH ABSORPTION SPECTROSCOPY

CROSS REFERENCE TO RELATED APPLICATIONS

This application claims the benefit under 35 U.S.C. § 119(e) of provisional Application No. 60/305,858, filed Jul. 18, 2001, the entire contents of which are herein incorporated by reference.

BACKGROUND OF INVENTION

1. Field of the Invention

The present invention relates to novel methods and systems for controlling the concentration of a component in a composition. The invention also relates to novel semiconductor processing methods and systems. The invention has particular applicability to the semiconductor manufacturing industry for online monitoring and control of the concentration of a corrosion inhibitor in a process chemical.

2. Description of the Related Art

Chemical mechanical planarization (CMP), also referred to as chemical mechanical polishing, and pre- and post-CMP storage and cleaning processes are commonly used in the manufacture of integrated circuits (ICs). To avoid corrosion of exposed metal during a metal CMP process, for example, for the planarization of copper-containing layers such as copper and copper-alloy layers, corrosion inhibitors such as benzotriazole, hydroquinone, tolyltriazole, imidazole, triazole, benzothiazole, mercaptobenzotriazole, gallic acid, pyragallol, catechol, recorsinol, etc., can be employed with the CMP slurry. In the CMP process, the corrosion inhibitor, typically in the form of a complex with the metal, passivates the metal surface of the wafer against chemical etching and allows uniform removal of the oxidized layer by mechanical action. The corrosion inhibitor complex also prevents the diffusion of oxygen into the wafer during subsequent, post-CMP cleaning operations. Liquid chemicals containing a corrosion inhibitor can also be used in a bath for storage or cleaning purposes before and/or after the CMP process to prevent corrosion of the metal surface.

It is desirable to maintain a known, constant concentration of the corrosion inhibitor in the CMP process and pre- and post-treatment baths in order to provide a manufacturable process. A decreased corrosion inhibitor level increases the likelihood of metal corrosion, whereas an increased concentration can result in corrosion inhibitor residue remaining on the wafer surface. These effects can result in a significant decrease in product yield. While off-line methods for measurement of the concentration of the corrosion inhibitors exist, such methods do not provide real-time feedback and control of the process.

Accordingly, there is a need in the art for methods and apparatuses for controlling the concentration of components such as a corrosion inhibitor in a CMP chemical and in pre- and post-CMP storage/treatment chemicals, which can provide real time, accurate process control in an easy and robust manner.

SUMMARY OF INVENTION

According to a first aspect of the invention, provided is method of controlling the concentration of a component in a composition, which involves: providing a composition containing a liquid portion, wherein the liquid portion comprises a component to be monitored; performing an absorption spectroscopy measurement on a sample of the composition; and controlling the concentration of the component in the composition based on the absorption spectroscopy measurement using a feedback control loop.

The component to be monitored can be, for example, a corrosion inhibitor, such as benzotriazole, tolyltriazole, imidazole, triazole, benzothiazole, mercaptobenzotriazole, hydroquinone, gallic acid, pyragallol, catechol, recorsinol, or a combination thereof. The concentration of the component in the composition can be controlled by adjustment of the amount of the component introduced into the CMP apparatus or by adjustment of the amount of a diluent introduced into the CMP apparatus. The absorption spectroscopy measurement can be, for example, a UV/visible light spectroscopy measurement.

According to a further aspect of the invention, provided is a semiconductor processing method. The method involves: contacting a semiconductor wafer with a solution containing a component to be monitored; controlling the concentration of the component by a method involving: performing an absorption spectroscopy measurement on a sample of the solution; and controlling the concentration of the component in the solution based on the absorption spectroscopy measurement using a feedback control loop.

In accordance with a further aspect of the invention, a system for controlling the concentration of a component in a composition is provided. The system includes: a source of a composition which has a liquid portion, wherein the liquid portion contains a component to be monitored; an absorption spectroscopy measurement apparatus for measuring the concentration of the component in a sample of the composition; and feedback control means for controlling the concentration of the component in the composition based on the absorption spectroscopy measurement.

The absorption spectroscopy system can have a plurality of measurement cells, as well as means for directing a sample to be measured to an appropriate measurement cell based on the amount of the component to be monitored.

In accordance with a further aspect of the invention, a semiconductor processing system is provided. The system includes: a chemical bath tank containing a solution for treating a semiconductor substrate; one or more conduits for introducing process materials into the chemical bath, the process materials containing a component to be monitored; an absorption spectroscopy measurement apparatus for measuring the concentration of the component in a sample of the solution; and feedback control means for controlling the concentration of the component in the solution based on the absorption spectroscopy measurement.

The methods and systems of the invention can effectively provide real-time, accurate process control, providing fast response time. The concentration of chemical species, which are otherwise not easily measurable using conventional techniques, can easily and accurately be determined.

BRIEF DESCRIPTION OF DRAWINGS

Other objects and aspects of the present invention will become apparent to one of ordinary skill in the art on a review of the specification, drawings and claims appended hereto, in which like reference numerals denote like features, and in which:

DETAILED DESCRIPTION

The invention provides methods and systems for monitoring and controlling the concentration of a component in a composition by use of absorption spectroscopy. While not being limited in any way thereto, the methods and systems can advantageously be used to monitor and control the concentration of a component of a composition used in a metal CMP process or in a pre- or post-CMP treatment process. Such compositions include, for example, metal CMP slurries and aqueous chemical compositions which contain a corrosion inhibitor, such as benzotriazole, tolyltriazole, imidazole, triazole, benzothiazole, mercaptobenzotriazole, hydroquinone, gallic acid, pyragallol, catechol, recorsinol, or a combination thereof. Any formulation can be analyzed with the condition that the component of interest in the formulation exhibits a discernible absorption signature in the wavelength range of the absorption system.

Figure 1:
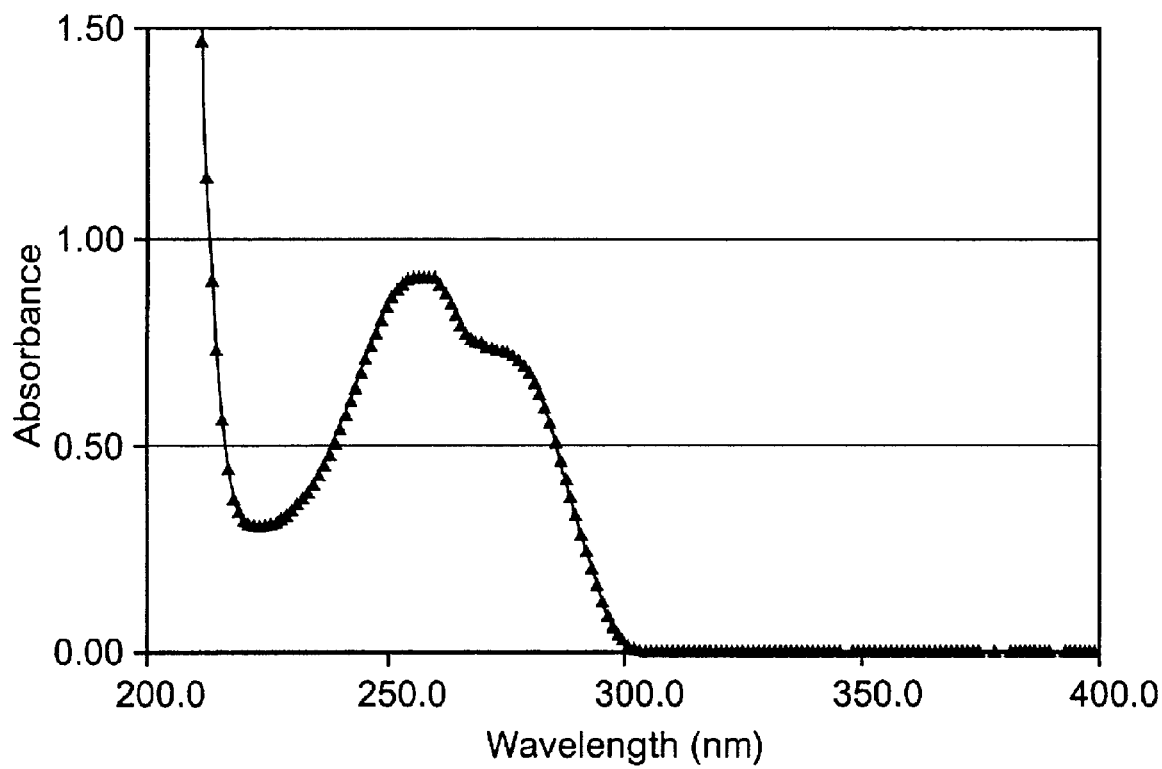
FIG. 1 is an absorption curve for benzotriazole.

The present invention operates on the basis of light absorption. The specific type of absorption spectroscopy system employed will depend, for example, on the particular species being monitored. The absorption spectroscopy method can track the absorbance or transmittance of light at a particular wavelength or wavelengths which is/are specific to the component of interest. In the case of benzotriazole, for example, the benzotriazole molecules in aqueous solutions absorb ultraviolet light at wavelengths of approximately 257 and 279 nm, with the relative magnitudes dependent upon the pH of the solution. FIG. 1 illustrates an absorption curve for benzotriazole which shows absorption peaks at these wavelengths. Within a narrow concentration range, the intensity of absorbed UV light is directly proportional to the amount of the component of interest in the sample and can be compared to a known standard to quantify the component's level in the sample.

Figure 2:
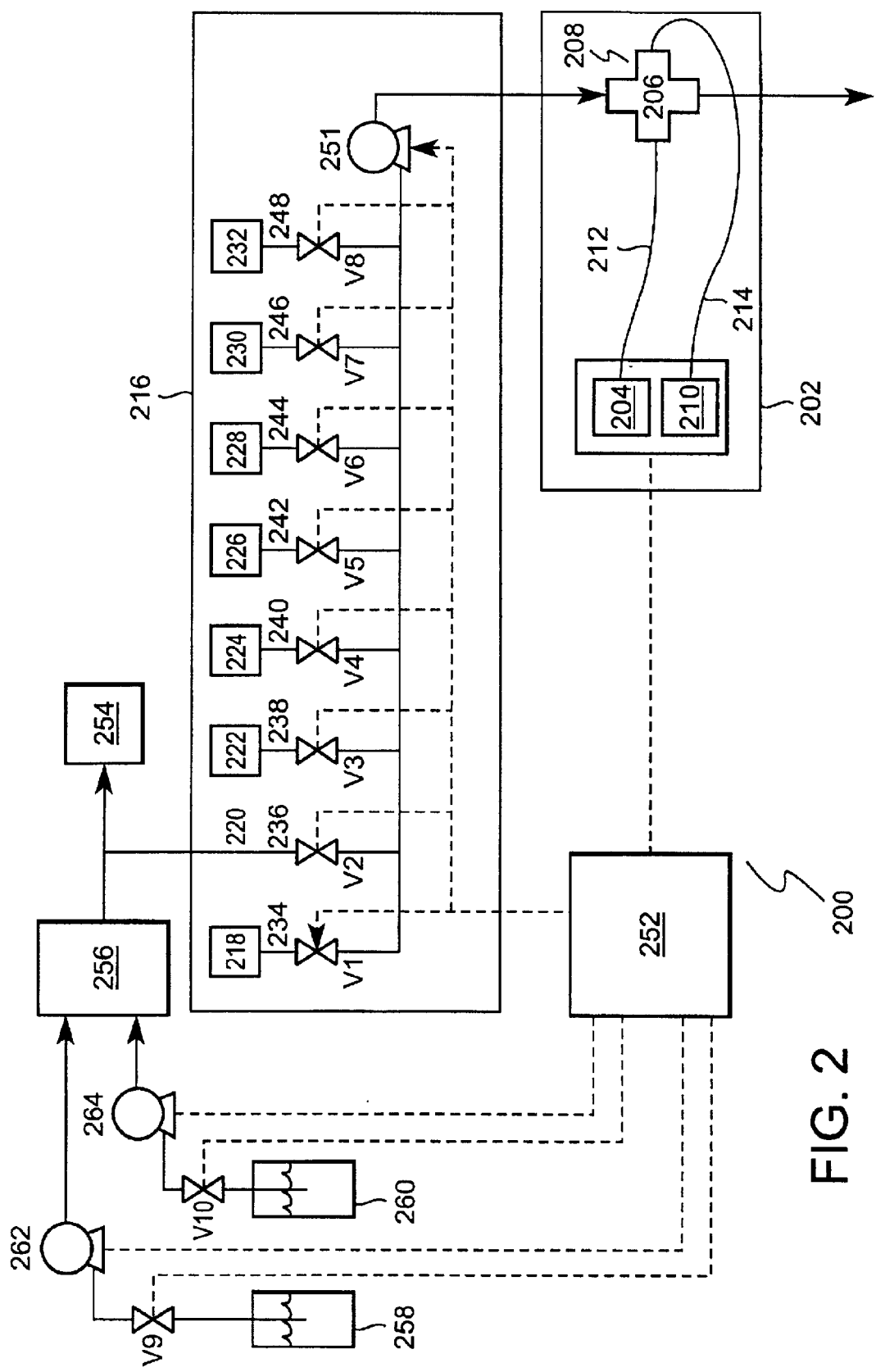
FIG. 2 illustrates an exemplary system in accordance with the invention.

The invention will now be described with reference to FIG. 2, which illustrates an exemplary system 200 for controlling the concentration of a component in a composition. Light absorption of the component of interest is measured with an absorption spectroscopy measurement system 202. Suitable systems are commercially available, for example, the Spectral Instruments (Tucson, Ariz.) Model 440 UV/Visible Spectrophotometer. The spectrometer employs a light source 204 that directs light through a sample region of a measurement cell 208 through which a sample of the composition to be measured flows. A detector detects the amount of light transmitted through the sample region. Fiber optic probes 212, 214 can be used to optically connect the light source and detector, respectively, with the sample region. The type of light source and detector will depend on the specific absorption spectroscopy technique employed. In the case of UV/visible light spectroscopy, for example, the light source can be a deuterium lamp and the detector a CCD array.

Figure 3:
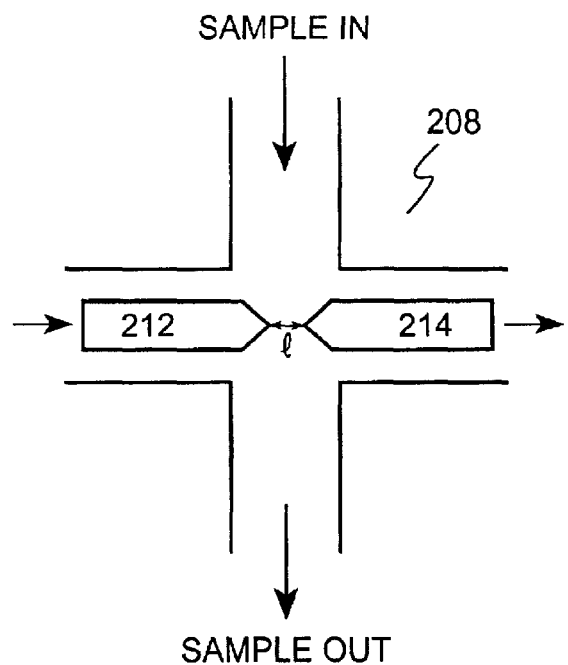
FIG. 3 is an enlarged view of the measurement cell shown in FIG. 2.

FIG. 3 is an enlarged view of the measurement cell The cell has a pathlength P, measured by the distance between the fiber optic probes 212 and 214. The pathlength is fixed during measurement. Detector electronics receive the output from the detector 210 and generate an output which is related to the absorbance of light at the particular wavelength. The measured absorbance is converted into a concentration of the component by a computer using known calibration data. Based on the measured absorbance, the concentration of the component of interest in the composition can be adjusted to a desired level.

The system further includes a sample distribution system 216 for alternately introducing samples of various chemicals into the measurement cell 208. These chemicals are fed from sources which can include, for example, de-ionized water 218, the subject composition being monitored 220, a check standard of known concentration, and a plurality of calibration standards 224, 226, 228, 230, 232 of known concentration. Each of the chemical sources is connected by a respective conduit 234, 236, 238, 240, 242, 244, 246, 248 and valve V1–V8 to a sample conduit which allow for introduction of the desired chemical sample into the measurement cell 208. A pump 251, typically a metering pump, is provided to assist transfer of the chemical sample through the system. Optionally, a dedicated pump shown) can be provided for each of the chemical sources in conduits 234, 236, 238, 240, 242, 244, 246, 248. In the various stages of operation, the sample line 250 and measurement cell 208 are typically flushed with the de-ionized water between samples by opening valve V1 for a predefined period of time, at which time valve V1 is closed.

Operation of the system is preferably automated by use of one or more controller 252 connected to the measurement system 202, the distribution system 216, and various other devices making up the system. The control system further can allow for the inputting of all of the system operating parameters including, for example, standard concentrations, acceptance criteria, valve timing, sample specifications, and data saving intervals, and can perform a data handling function. Suitable control means are known in the art, and include, for example, one or more programmable logic controllers (PLCs) and/or microprocessors. Automatic control of the various valves, pump and other flow control devices can be effected based on the analysis data from the measurement system. Signals are sent from the measurement system 202 to the controller 252 and from the controller to the pump and valves of the distribution system 216 as shown by the dashed lines. The particular material flowing through the sample conduit 250 and into the measurement cell 208 at any given time will depend on the stage of operation of the measurement system, with three separate stages of operation preferably being provided. These stages include a calibration stage, a check standard stage, and a sample measurement stage, described below.

Figure 4:
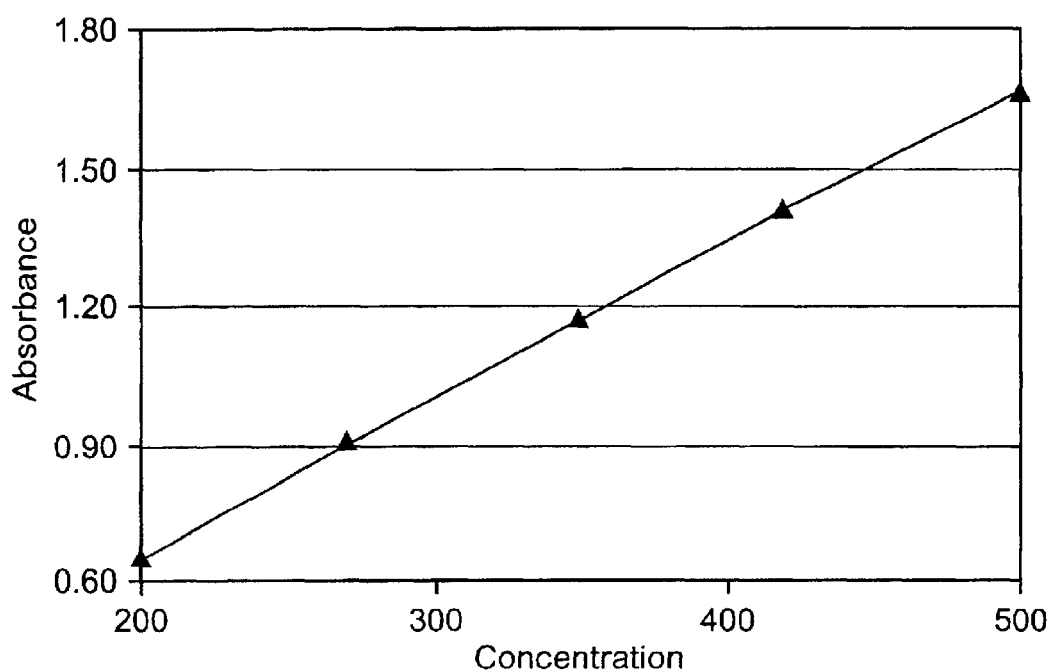
FIG. 4 is a calibration curve obtained for benzotriazole with the system in accordance with the invention.

In the calibration stage, the measurement system is periodically calibrated for the component of interest over a desired concentration range using the plurality of calibration standards 224, 226, 228, 230, 232. A calibration curve is generated by analyzing each of the standard calibration samples and plotting the absorbance of each at the characteristic wavelength versus the concentration. FIG. 4 is an exemplary calibration curve obtained for benzotriazole using five standard samples, with absorbance being plotted versus concentration, in ppm (parts-per-million). To generate this curve, the calibration standards 224, 226, 228, 230, 232 are sequentially introduced into the measurement cell 208 and analyzed by opening the corresponding valve V4–V8, respectively.

An exemplary calibration stage which can be employed in the invention will now be described. The pump 251 is turned on and valve V1 is opened to allow the de-ionized water to flow from source 218 through conduit 234 into the sample conduit 250 and through the measurement cell 208. A shutter covering the light source 204 is opened to allow light to pass through the de-ionized water in the sample region 206 and back to the detector 210 to "blank" the instrument. The absorbance of the water is set to zero at the characteristic wavelength, and any increase in absorbance in subsequent testing can be attributed to the presence of the component of interest. Valve V1 is closed after a predefined period of time. Valve V4 is then opened, and the first calibration standard 224 is pumped through the measurement cell and the absorbance is recorded. The absorbance is preferably measured a plurality of times and the average value is recorded if the standard deviation is within a predefined acceptance criterion range. Once the first calibration standard 224 has been analyzed, valve V4 is closed and valve V1 can be reopened to allow the line to be flushed with de-ionized water. After flushing, valve V5 is opened and second calibration standard 226 is pumped through the measurement cell 208 and analyzed in the same manner as the first calibration standard. The same flushing and analysis routine is performed for the remaining calibration standards 228, 230, 232.

An alarm can be provided which can alert the user with an error message to check the standard solution in the event one or more of the calibration standards measures at too low or too high of a concentration. For example, if the measured absorbance for a calibration standard is 0 or greater than 2, an alarm alerting the user to refill the calibration standard container can be provided. Once the calibration standards have all been evaluated, software typically plots the measured absorbance versus concentration for the standards and fits a line to the data as shown in FIG. 4. Predefined acceptance criteria for the quality of fit of the calibration curve are typically an input parameter in the control system. If the fit meets the predefined limits, the calibration is accepted.

The check standard stage is typically run after the calibration stage and before the sample measurement stage to verify that the measurement instrument is accurately determining the concentration and is properly calibrated. In the check standard stage, a standard solution containing the component of interest of a known target concentration is allowed to flow from the check standard source 222 through the measurement cell 208 by opening valve V3. The concentration of the check standard sample is then determined, with the measurement preferably being repeated a plurality of times. If the measured concentration and standard deviation (in the case of multiple measurements) are within predefined range limits, the calibration is accepted and the sample measurement stage can proceed. If, however, the measured concentration and/or standard deviation are not within the predefined range limits, this indicates that the instrument is not in calibration and a sample failure alarm, for example, a visual and/or aural alarm, activates. Valve V1 is then opened to flush the line with de-ionized water, the pump 251 is turned on, and the calibration stage can be re-initiated Thus, the same calibration curve is used until a check standard mode measures outside of the predefined range.

In the sample measurement stage, a sample of the composition containing an unknown concentration of the component of interest is analyzed by the measurement system 202. Advantageously, once the calibration routine has been run successfully, the composition stream can be continuously analyzed for an extended period of time, typically for several days, without the need for re-calibration. The composition is analyzed by opening valve V2, thus allowing the sample to flow from source 220 to the measurement cell 208. The intensity of the light measured by the detector 210 is compared with the intensity observed with the deionized water blank sample and the calibration standards to arrive at a measured concentration for the component of interest.

The sample can, for example, be taken from a point in a chemical distribution system upstream or downstream from a point of use 254. Typically, the sample is taken from a point upstream or downstream from a CMP process or from a bath for storage or cleaning purposes before and/or after a CMP process, or from the CMP tool or bath itself. In the case the composition is in the form of a slurry, a separation unit, for example a centrifuge or filter, should be used to remove any solids from the composition prior to analysis of the liquid. In one exemplary aspect of the invention, the sample can be taken from a point upstream from the point of use 254 and downstream from a chemical blending unit 256, with feedback from the measurement system being used to control the introduction of chemicals from sources 258, 260 into the blending unit by controlling one or both of pumps 262, 264. Blending units which can be employed with the invention are described, for example, in U.S. application Ser. No. 09/468,411, filed Dec. 20, 1999, the entire contents of which are incorporated herein by reference. The system allows the user to make immediate adjustments to the blend system to compensate for variations in concentration of the component of interest in the composition. With the system operating at the point of dispense, it is possible to verify that with each blend, compositions within specification are being delivered to the point of use.

Figure 5:
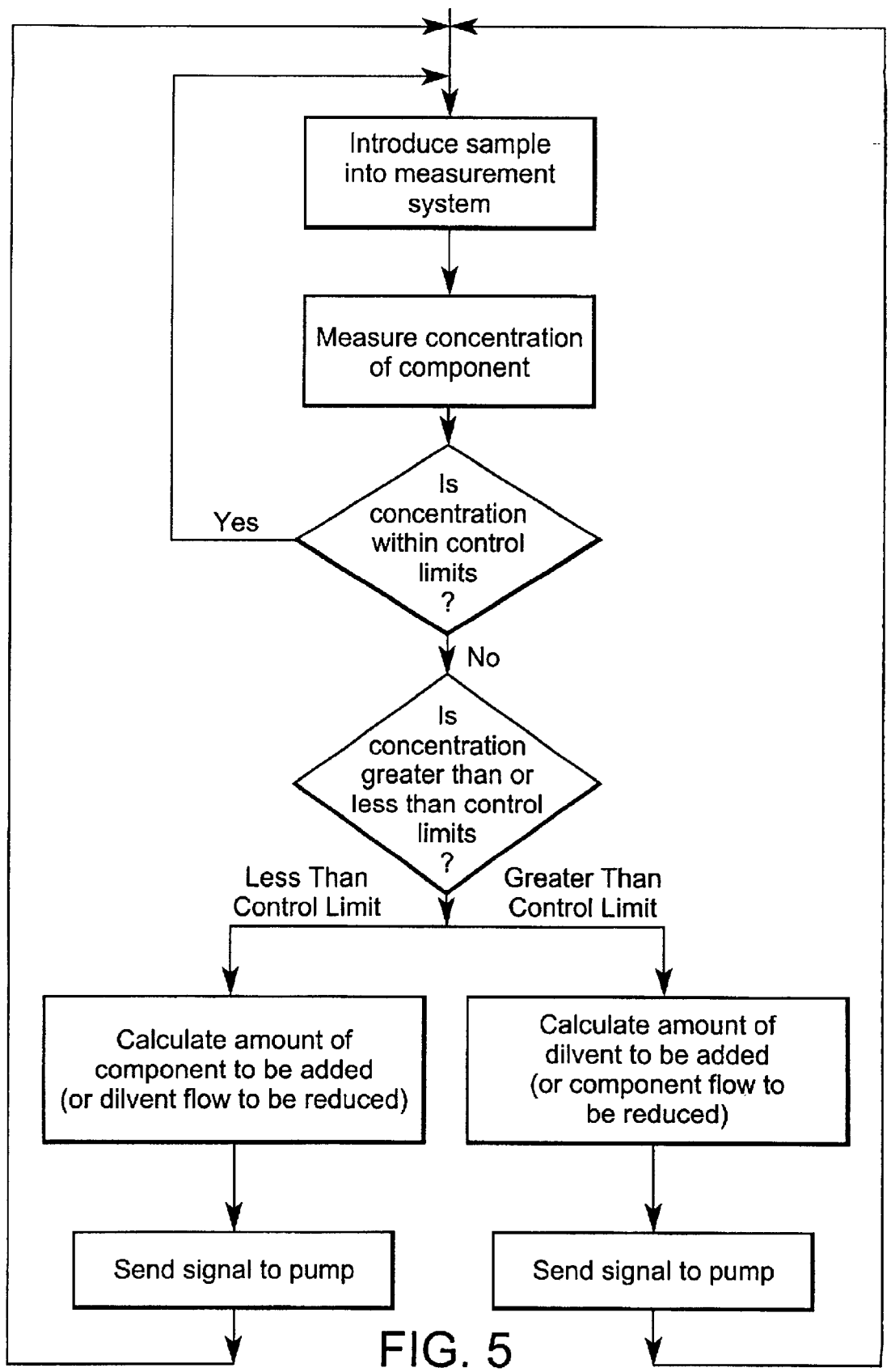
FIG. 5 is an exemplary logic flowchart for a sample measurement stage which can be used in the invention.

In controlling the compositions, logic such as shown in FIG. 5 can be employed. A sample of the composition is first introduced into the sample region of the measurement cell and the concentration is measured. The value of the concentration is compared against the predefined control limits which can be programmed into the analysis software. Based on the measurement results, the concentration of the component of interest in the composition can be automatically controlled to a predefined target value. If the measured concentration is within the control limits, another sample can be introduced into the measurement cell if further monitoring is desired.

If the measured concentration is not within the control limits, the component of interest, deionized water, or other chemical in the composition can be increased or reduced as needed. If the concentration of the component is too low, the controller 252 can calculate the requisite amount of the component in source 258 to be added and send a control signal to the pump 262 and valve V9. Optionally, the desired concentration can be achieved by reducing the amount of diluent being introduced from source 260 relative to the component by sending a control signal to the pump 264 and valve V10. If the measured concentration of the component is too high, the controller 252 can similarly calculate and cause to be added the requisite amount of diluent or by reducing the amount of the component being introduced relative to the diluent. Optionally, the feedback signal from the measurement system 202 can be coupled with a feedback signal from a weigh scale or volume sensor to derive the amount of the component of interest (or diluent) that is required to be added to maintain the component concentration within the predefined control limits. In this way, the measured value of concentration can be used for real-time control of the component's concentration in the composition.

The apparatuses and methods of the invention can advantageously provide continuous monitoring and control of the concentration of the component of interest at a plurality of sampling locations. Since the concentration at different sampling locations may vary by several orders of magnitude, the measurement system preferably has the capability of measurement over a wide concentration range. One technique for sample measurement where the absorbance value is greater than that provided by the calibration curve is to dilute the sample by addition of deionized water by a known dilution factor. The concentration can then be determined using the calibration curve, taking into account the dilution factor. Alternatively, if the absorbance value is above the calibration range and dilution of the sample stream is undesirable, the optical path length can be reduced to decrease the measured absorbance of the sample.

A further technique for multi-point measurement involves provision of a plurality of measurement cells measuring samples taken from various points of a process. This will allow for each measurement cell to be optimized for a given target concentration range. The number and specifics of cells will depend on the range of concentrations to be measured. The cells can each be configured with a different pathlength to allow measurement of the component of interest in different concentration ranges. This follows from Beer's Law. The cell pathlength can thus be varied to achieve the desired absorbance at each of the target concentration levels. With the use of fiber optic probes, the pathlength can be conveniently varied by moving the probes either closer together or further apart. The system is capable of automatically switching between the measurement cells to the cell having the most appropriate pathlength for the sample being measured. For this purpose, control algorithms can be employed which appropriately divert the sample flow based on the absorbance measurements. The same effect obtained with a multiple measurement cell configuration can be achieved by use of a single measurement cell having an automatically adjustable pathlength.

Figure 6:
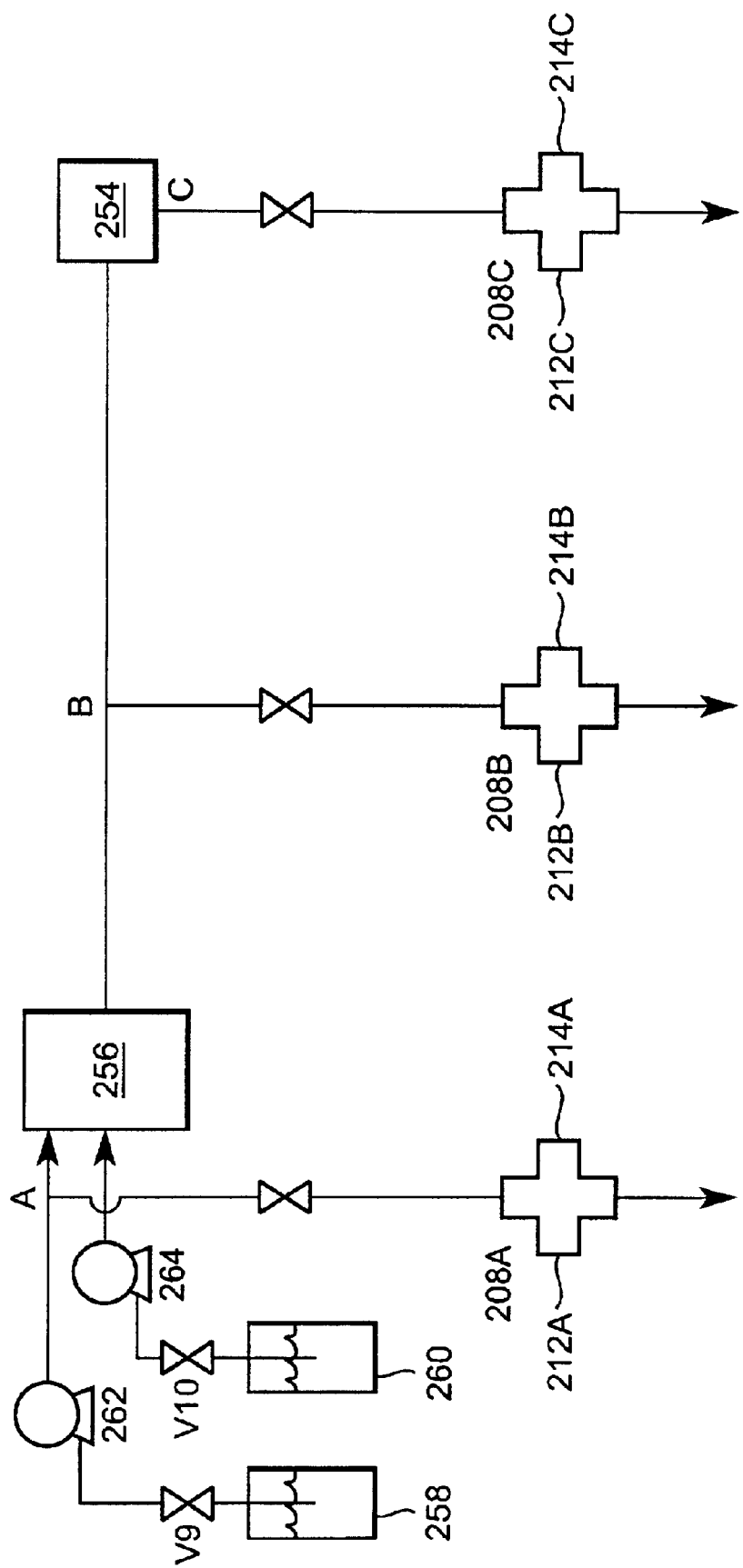
FIG. 6 illustrates a design for multi-point sampling and control of a component in accordance with the invention.

Multi-point measurement can be applied, for example, to sample analysis at various points in a chemical distribution system. In the case of a CMP process, for example, this control can take place at the platen and tubs of the CMP tool, or in a process before or after the CMP process. FIG. 6 illustrates a portion of a multi-point measurement system 600 which can form part of the systems described above. A chemical distribution system includes chemical sources 258, 260 which feed into a dilution station/chemical blending unit 256, which in turn is connected to a point of use 254. Sampling points are located at locations A, B, and C, with measurement cells 208A, 208B, 208C, respectively, being provided for sample measurement from those sampling points. The concentrations at points A, B and C are typically very different. For example, in the case of a benzotriazole corrosion inhibitor solution for use in a pre- or post-CMP chemical bath, a typical concentration at point A is about 5 wt %, at point B about 300 ppm, and at point C about 10 ppm. Thus, the concentration at point A is greater than that at point B, and that at point B is greater than that at point C. A suitable pathlength of the measurement cell for monitoring at point A would thus be less than that for monitoring at point B, and the pathlength of the cell for monitoring at point C would be greater than that for monitoring at point B.

A source of a corrosion inhibitor 258 and other chemical source 260, for example, deionized water, are connected to the dilution station/blending unit 256 in which the corrosion inhibitor is diluted with the water or other chemical(s) to a desired concentration. The dilution station 256 is connected to the point of use 254, for example, a CMP tool or treatment bath, for introducing the chemical thereto. The chemical can be further diluted at the point of use. The concentration of the corrosion inhibitor can be monitored at the one or more sampling points A, B and C, with the corrosion inhibitor alone being monitored at point A by measurement cell 208A, the first level of dilution at point B being monitored by measurement cell 208B, and the second level of dilution at point C being monitored by measurement cell 208C. Control signals based on the measurements as points A, B, and/or C can be fed back to control the concentration of the corrosion inhibitor.

The methods and systems in accordance with the invention provide for rapid and accurate measurement as well as real-time process control over a wide range of concentrations. Additionally, the systems are easily maintained and possess a relatively small footprint, making it suitable for location in a semiconductor wafer fabrication facility at or near the point of use of the chemical.

While the invention has been described in detail with reference to specific embodiments thereof, it will be apparent to those skilled in the art that various changes and modifications can be made, and equivalents employed, without departing from the scope of the appended claims.

What is claimed is:

1. A semiconductor processing method, comprising:
    contacting a semiconductor wafer with a solution comprising a component to be monitored;
    controlling the concentration of the component by a method comprising:
        performing an absorption spectroscopy measurement on a sample of the solution; and
        controlling the concentration of the component in the solution based on the absorption spectroscopy measurement using a feedback control loop.

2. The method according to claim 1, wherein the component to be monitored is a corrosion inhibitor.

3. The method according to claim 2, wherein the corrosion inhibitor is benzotriazole, tolyltriazole, imidazole, triazole, benzothiazole, mercaptobenzotriazole, hydroquinone, gallic acid, pyragallol, catechol, recorsinol, or a combination thereof.

4. The method according to claim 1, wherein the concentration of the component in the solution is controlled by adjustment of the amount of the component introduced into the solution.

5. The method according to claim 1, wherein the concentration of the component in the solution is controlled by adjustment of the amount of a diluent introduced into the solution.

6. The method according to claim 1, wherein the absorption spectroscopy measurement is a UV/visible light spectroscopy measurement.

7. The method according to claim 1, further comprising transporting the sample of the solution using a pump.

8. A semiconductor processing system, comprising:
    a chemical bath tank containing a solution for treating a semiconductor substrate;
    one or more conduits for introducing process materials into the chemical bath, the process materials comprising a component to be monitored;
    an absorption spectroscopy measurement apparatus for measuring the concentration of the component in a sample of the solution; and
    feedback control means for controlling the concentration of the component in the solution based on the absorption spectroscopy measurement.

9. The system of claim 8, wherein the absorption spectroscopy system comprises a plurality of measurement cells.

10. The system of claim 8, further comprising means for directing the sample to an appropriate measurement cell depending on the concentration of the component to be monitored in the sample.

11. The system according to claim 8, wherein the component to be monitored is a corrosion inhibitor.

12. The system according to claim 11, wherein the corrosion inhibitor is benzotriazole, tolyltriazole, imidazole, triazole, benzothiazole, mercaptobenzotriazole, hydroquinone, gallic acid, pyragallol, catechol, recorsinol, or a combination thereof.

13. The system according to claim 8, wherein the absorption spectroscopy measurement system is a UV/visible light spectroscopy measurement system.

14. The system according to claim 8, further comprising a pump disposed between the chemical bath tank and the absorption spectroscopy measurement apparatus.

\* \* \* \* \*